000
United States Patent [19]

Fedi et al.

[11] Patent Number: 4,544,556

[45] Date of Patent: Oct. 1, 1985

[54] XANTHINE DERIVATIVES, PHARMACEUTICAL COMPOSITIONS CONTAINING SAME AND THEIR THERAPEUTIC USE

[75] Inventors: Mauro Fedi, Sesto Fiorentino; Graziano Bonacchi, Pistoia, both of Italy

[73] Assignee: Malesci S.p.A. Istituto Farmacologico, Florence, Italy

[21] Appl. No.: 520,272

[22] Filed: Aug. 4, 1983

[30] Foreign Application Priority Data

Aug. 10, 1982 [IT] Italy .................................. 48970 A/82

[51] Int. Cl.$^4$ ..................... C07D 473/08; A61K 31/52

[52] U.S. Cl. ..................................... 514/263; 544/267; 544/273

[58] Field of Search ................. 544/267, 273; 426/253

[56] References Cited

U.S. PATENT DOCUMENTS 4,299,833  11/1981  Philoppossian et al. ............ 544/267

Primary Examiner—Nicholas S. Rizzo
Attorney, Agent, or Firm—Beveridge, DeGrandi & Weilacher

[57] ABSTRACT

Alkyl-substituted xanthines having a prevailingly peripheral theophylline-assimilated activity, process for their preparation, pharmaceutical compositions containing said xanthines and their therapeutic use.

12 Claims, No Drawings

XANTHINE DERIVATIVES, PHARMACEUTICAL COMPOSITIONS CONTAINING SAME AND THEIR THERAPEUTIC USE

The invention concerns alkyl-substituted xanthines having a prevailingly peripheral theophylline-assimilated acitivity, the process for their preparation, the pharmaceutical compositions containing said xanthines and their therapeutic use.

More specifically, the invention relates to compounds having the general formula (1):

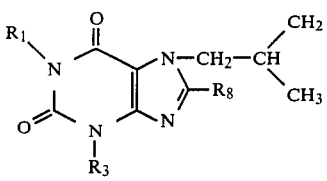

wherein
- $R_1 = H; CH_3$
- $R_3 = C_NH_{2n+1}$, n is 1 to 5
- $R_8 = H; CH_3$.

The alkyl group $R_3$ of general Formula (1) preferably includes: methyl, n-propyl, isobutyl, 2-methylbutyl.

The compounds according to the invention are characterized by a theophylline-assimilated activity which is prevailingly a peripheral one due to the presence of isobutyl chain in the 7 position. Therefore said compounds may be used, for inst., in the bronchospastic affections of different ethiopathogenesis, with reduced central side-effects with respect to theophillyne.

The compounds can be conveniently prepared in the form of pharmaceutical compositions as tables, capsules, retarded release tablets, suppositories, vials, syrups, drops, aerosol and ointments.

The oral administration preparates may contain diluents, lubricants, bindings, disintegrating agents, dyes, flavourings, surfactants, preservatives, buffers and the like.

In particular, the excipients can include cellulose,- mannitol,lactose and like; the starch disintegrators and their derivatives, polyvinylpyrrolidone and like and the lubricants as stearic acid, magnesium lauryl-sulphonate and like.

The present invention concerns also process for preparing compounds of Formula (1), by reacting a salt of the compound having the Formula (II).

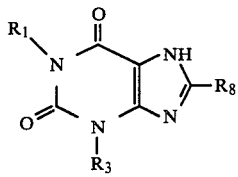

wherein $R_1$, $R_3$ and $R_8$ have the same meanings mentioned for the above Formula (I) with an isobutyl halide in a solvent suited thereto.

The salts of compounds having Formula (II) may be sodium salts or potassium salts and may be prepared separately or during the reaction by means of alkaline metal hydrides or alcoholates or hydroxides.

The following example gives a further non limitative illustration of the invention

EXAMPLE 1,3-dimethyl-7-isobutyl-xanthine(7-isobutyl-theophylline)

18 g of theophylline (0.1 moles) are dissolved in 200 ml of N,N-dimethylformamide and treated under stirring and cooling, with 2.4 g (0.1 moles) of NaH.

When the salification is completed, 13.7 Kg of isobutyl bromide are added slowly and the mixture is heated at 80° C. for 3 hours. The solvent is distilled under vacuum and the residuum is treated with water and ether. The ether extract is dry concentrated and residuum crystallized from hexane.

m.p. = 88°/90° C., yield: 75%

The chemical structure is confirmed by the elementary analysis and the NMR test data.

An analogous process consents to obtain the following compounds:
- 1-methyl-3-isobuty-7-isobutyl xanthine: m.p.=66°/68° C.; Yield=60%
- 1-methyl-3-(2-methyl-butyl)-7-isobutyl-8-methyl-xanthine: m.p.=190° C.; 0.1 mm Hg; Yield=60%
- 1-methyl-3-(2-methyl-butyl)-7-isobutyl-8-methyl-xanthine: m.p.=69°/71° C.; Yield=55%
- 3-(n-propyl)-7-isobutyl xanthine: m.p.=158°/160° C.; Yield=40%

As an example the pharmaceutical—toxicological outline of the 7-isobutyl theophillyne is summarized hereinbelow.

Acute Toxicity

The compound has been administered either per os or by intravenous injection to male Swiss mouses having a weight of about 20 g, empty since 16 hours.

The $DL_{50}$ values have resulted of 199 mg/kg and 129 mg/kg, respectively.

Antibronchospastic Activity

The test has been carried out in anaesthesized adult guinea pigs under artificial respiration.

The bronchospasm induced by acetylcholine e.v. has been measured according to the H. KONZETT and R. ROSSLER method (Arch. Exp. Pharmakol. 195, 71; 1940) by means of a transducer sidewise connected to the inhalating tube.

The $ED_{50}$ (the dose which represents a 50% reduction of acetylcholine induced bronchospasm) has been tested at different intervals after the product has been administered by intramuscular way and in comparison with the theophylline administration.

|  | $ED_{50}$ mmoles/kg 7-isobutyl theophylline | Theophylline |
| --- | --- | --- |
| 30' | 0,12 | 0,27 |
| 60' | 0,14 | 0,23 |
| 90' | 0,16 | 0,20 |

Antiphosphodiesterase Activity

The preparation of the enzyme from heart, lungs and brain of Wistar rats and the activity test of P.D.E. have been carried out according to the R. W. BUTCHER and E. W. SUTHERLAND (J. Biol. Chem. 237, 1244; 1962).

In comparison with theophylline the invention derivative has resulted twice more active against brain P.D.E. and four times more active against the heart and lung ones.

Activity On CNS

The effect of the S.C. treatment (20') with theophylline and 7-isobutyl theophylline on the reaction to subtoxic dose of cardiazole i.p. 60-70 mg/Kg has been carried out indifferent animal species.

| Product | Dose mg/kg | % dead animals | | |
|---|---|---|---|---|
| | | mouses | rats | guinea pigs |
| controls | | 0 | 0 | 0 |
| Theophylline | 12,5 | 10 | | |
| | 25 | 20 | | |
| | 50 | 60 | 100 | 100 |
| | 100 | 100 | | |
| 7-isobutyl theophylline | 25 | 0 | | |
| | 50 | 0 | 0 | 0 |
| | 100 | 0 | 0 | 0 |

The present invention has been described with a particular reference to specific embodiments, but it is to be understood that changes and modifications may be carried out within the relevant protection scope.

We claim:

1. A compound of the formula

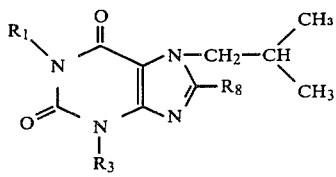

wherein
$R_1 = H; CH_3$
$R_3 = C_nH_{2n+1}$
$R_8 = H; CH_3$
n is 1 to 5.

2. Compound according to claim 1, wherein $R_1 = R_3 = $ methyl; $R_8 = H$.

3. Compound according to claim 1, wherein $R_1 = $ methyl, $R_3 = $ isobutyl, $R_8 = H$.

4. Compound according to claim 1, wherein $R_1 = $ methyl, $R_3 = $ 2-methylbutyl, $R_8 = H$.

5. Compound according to claim 1, wherein $R_1 = $ methyl, $R_3 = $ 2-methylbutyl, $R_8 = $ methyl.

6. Compound according to claim 1, wherein $R_1 = R_8 = H$, $R_3 = $ n-propyl.

7. A pharmaceutical composition containing an effective quantity of a compound of the formula

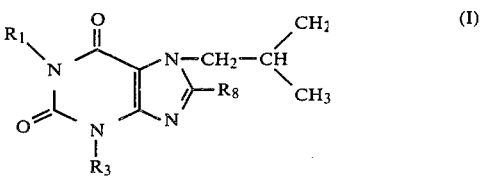

wherein
$R_1 = H; CH_3$
$R_3 = C_nH_{2n+1}$
$R_8 = H; CH_3$
n is 1 to 5, in combination with an inert pharmaceutically acceptable carrier to produce an antibronchospastic or antiphosphodiesterase effect.

8. Pharmaceutical composition according to claim 7, wherein $R_1 = R_3 = $ methyl; $R_8 = H$.

9. Pharmaceutical composition according to claim 7, wherein $R_1 = $ methyl, $R_3 = $ isobutyl, $R_8 = H$.

10. Pharmaceutical composition according to claim 7, wherein $R_1 = $ methyl, $R_3 = $ 2-methylbutyl, $R_8 = H$.

11. Pharmaceutical composition according to claim 7, wherein $R_1 = $ methyl, $R_3 = $ 2-methybutyl, $R_8 = $ methyl.

12. Pharmaceutical composition according to claim 7, wherein $R_1 = R_8 = H$, $R_3 = $ n-propyl.

* * * * *